United States Patent [19]

Byrne et al.

[11] Patent Number: 5,221,778
[45] Date of Patent: Jun. 22, 1993

[54] MULTIPLEX GENE REGULATION

[75] Inventors: Guerard W. Byrne, Hamden; Frank H. Ruddle, New Haven, both of Conn.

[73] Assignee: Yale University, New Haven, Conn.

[21] Appl. No.: 236,102

[22] Filed: Aug. 24, 1988

[51] Int. Cl.$^5$ .............................................. C12N 15/00
[52] U.S. Cl. .................. 800/2; 800/DIG. 1; 800/DIG. 4; 435/172.3; 435/317.1; 435/948; 935/111; 424/89
[58] Field of Search ............ 536/27; 800/1, 2, DIG. 1, 800/DIG. 4; 435/320, 317.1, 172.3, 948; 935/111; 424/89

[56] References Cited

U.S. PATENT DOCUMENTS 4,736,866  4/1988  Leder et al. .............................. 800/2
4,873,191 10/1989  Wagner et al. ..................... 435/172.3

OTHER PUBLICATIONS

Van Brunt, Biotech. 6: 1149, 1151, 1152, 1154 (1988).
Wilmut et al., New Scientist 7: 56–59 (1988).
Overbeek et al., Science 231: 1574–7 (1986).
Julien et al., Mol. Brain Res. 1: 243–250 (1986).
Jaenisch, Science 240: 1468–1474 (1988).
Hinrichs, S., et al, "A Transgenic Mouse Model for Human Neurofibromatosis" *Science*, vol. 237, 1340–1343.
Nerenberg, M., "The tat Gene of Human T-Lymphotropic Virus Type 1 Induces Mesenchymal Tumors in Transgenic Mice", *Research Articles*, Sep. 1987, II pp. 1324–1329.
Gorman, C., "Recombinant Genomes Which Express Chloramphenicol Acetyltransferase in Mammalian Cells", *Molecular and Cellular Biology*, Sep. 1982, pp. 1044–1051.
O'Hare, Peter, "Comparison of Upstream Sequence Req. for Pos. and Neg. Reg. of Herpes Simplex Virus Immed-Early Gene by 3-Vir. Encoded trans-Acting Factors", *Journal of Virology*, Jan. 1987, pp. 190–199.
O'Hare, et al, "3 trans-Acting Reg. Proteins of Herp. Sim. Virus Modulate Immed.-Early Gene Exp. in Pathway Inv. Pos. and Neg., Feedback Reg.", *Journal of Virology*, Dec. 1985, pp. 723–733.
*Nucleic Acids Research*, vol. 16, #4, 1988, pp. 1423–1430.

Primary Examiner—Jasemine C. Chambers
Attorney, Agent, or Firm—Sprung Horn Kramer & Woods

[57] ABSTRACT

A transgenic mouse offspring produced by the mating of a first transgenic mouse carrying a transresponder transgene whose expression is regulated by a viral gene product of HSV-1 and a second transgenic mouse carrying a transactivator transgene. A process for expressing a gene of interest which comprises the mating of a first transgenic mouse carrying a transresponder transgene whose expression is regulated by a viral gene product of HSV-1 and a second transgenic mouse carrying a transactivator transgene.

12 Claims, 9 Drawing Sheets

HSV-1 TIF GENE     HSV-1 IE PROMOTER

CAT GENE    ──── VECTOR SEQUENCES

MULTIPLEX GENE REGULATION

GOVERNMENT RIGHTS

This invention was made with United States Government support under Grant No. F 32 GM 11818-02 from the National Institute of Health ("NIH"). The United States Government has certain rights in this invention.

BACKGROUND OF THE INVENTION

1. Field of the Invention

The present invention concerns a Multiplex Gene Regulatory ("MGR") system which involves a two component process which provides a method of gene regulation and induction in trangenic animals.

2. Background Information

Heretofore there were two basic approaches used to control transgene expression. Heretofore either inducible promoters (Palmiter, R.D., Brinster, R.L., Hammer, R.E., Trumbauer, M.E., Rosenfeld, M.G., Birnberg, N.C. and Evans, R.M., (1982), "Dramatic Growth of Mice that Develop from Eggs Microinjected with Metallothionein-Growth Hormone Fusion Genes", *Nature*, 300, 611–615; Stewart, T.A., Patttengale, P.K. and Leder, P., (1984), "Spontaneous Mammary Adenocarcinomas in Transgenic Mice that Carry and Express MTV/myc Fusion Genes, *Cell*, 38, 627–637; Hanahan, D., (1985), "Heritable Formation of Pancreatic B-cell Tumors in Transgenic Mice Expressing Recombinant Insulin/simian Virus 40 Oncogenes", *Nature*, 315, 115–122) or tissue specific promoter elements (Swift, G.H., Hammer, R.E., MacDonald, R.J. and Brinster, R.L., (1984), "Tissue-specific Expression of the Rat Pancreatic Eleastase 1 Gene in Transgenic Mice, *Cell*, 38, 639–646; Palmiter, R.D., Behringer, R.R., Quaife, C.J., Maxwell, F., Maxwell, I.H. and Brinster, R., (1987), "Cell Lineage Ablation in Transgenic Mice by Cell-specific Expression of a Toxin Gene", *Cell*, 50, 435–443); Overbeek, P.A., Chepelinsky, A.B., Khillan, J.S., Piatigorsky, J. and Westphal, H., (1985), "Lens Specific Expression and Developmental Regulation of the Bacterial Chloramphenicol Acetyltransferase Gene Driven by the Murine Alpha A-crystallin Promoter in Transgenic Mice", *Proc. Natl. Acad. Sci.*, 82, 7815–7819) have been used to regulate genes in transgenic mice. These are single tiered regulatory systems. Regulation by either inducible or tissue specific promoters results in some level of basal transgene expression which cannot be experimentally controlled. Regulation by tissue specific promoters merely directs expression to a certain tissue or organ and does not provide a direct means for controlling gene expression.

Inducible promoters provide a method to manipulate the time of gene expressions however, this approach lacks a high degree of tissue specificity. In addition, inducible promoters are generally active during certain developmental stages. The basal activity level cannot be experimentally controlled. Thus these systems suffer from either lack of tissue specificity, endogenous basal activity (inducible promoters) or a lack of inducibility (tissue specific promoters).

Recently Jaspal S. Khillan, Keith C. Deen, Shu-hua Yu, Raymond W. Sweet, Martin Rosenberg and Heiner Wetphal, "Gene Transactivation Medicated by the TAT Gene of Human Immunodeficiency Virus in Transgenic Mice", *Nucleic Acids Research*, Volume 16, Number 4, 1988, 1423–1430, have used the long terminal repeat (LTR) and the tat gene of the Human Immunodeficiency Virus (HIV) to construct a two tiered regulatory system. In their system the LTR is transactivated by the tat gene product. However, the LTR-CAT transgene was active in the thymus, eye, spleen, small intestine and liver in the uninduced state. The high basal activity of the HIV LTR severely limits the utility of the Khillan et al system.

In addition to the transactivation of HIV, the tat transactivation of HTLV-1 has been introduced into mice. Transgenic mice which express the HTLV-1 tat gene is described in Michael Nerenberg, Steven H. Hinrichs, R. Kay Reynolds, George Khoury and Gilbert Jay, "The tat Gene of Human T-Lymphotropic Virus Type I Induces Mesenchymal Tumors in Transgenic Mice", *Science*, 237, 1324–1329, Sep. 11, 1987 and Steven H. Hinrichs, Michael Nerenberg, R. Kay Reynolds, George Khoury and Gilbert Jay, "A Transgenic Mouse Model for Human Neurofibromatosis", Science, 237, 1340–1343, Sep. 11, 1987. These two papers point out that placing viral transactivator genes in mice can yield unpredictable results, and that only some transactivator genes will be useful for controlling gene expression in transgenic non-human mammals.

Transgenic non-human mammals is the subject of U.S. Pat. No. 4,736,866 to Leder et al.

To use transgenic animals for the analysis of gene function or to produce desirable gene products it is necessary to regulate the expression of the gene in a controlled and predictable manner. Ideally one would like to control both the time and site of expression in order to maintain the highest degree of experimental and marketing flexibility. The present invention, by utilizing a two-tiered system of control, provides the necessary degree of gene regulation required to obviate the aforesaid problem.

DEFINITIONS

MGR System—MGR System - Multiplex Gene Regulatory system

TR—transresponder, transgenic non-human line which carries the gene of interest

TA—transactivator, transgenic non-human line which carries the gene which produces the required transactivator; regulated by any promoter sequence; including the promoter normally associated with the gene in the TR line Promoter—regulatory sequence which controls gene expression IE—immediate early promoter from HSV-1

TIF—trans-inducing factor or transactivator from HSV-1

IE-CAT—a transgenic mouse line

NFT—a transgenic mouse line

CAT—chloramphenicol acetyltransferase gene

NF-L—mouse neurofilament gene (also may be referred to herein as "NF")

HSV-1—Herpes Simplex Virus Type 1

LTR—long terminal repeat

HIV—human immunodeficiency virus pIE—plasmid which contains the IE sequence

BPV—bovine papillomavirus

CRPV—cottontail rabbit papillomarvirus

EBV—Epstein-Barr virus

HPV—human papillomavirus

EGF—epidermal growth factor

EPO—erythropoitin

FGF—fibroblast growth factor

G-CSF—granulocyte colony stimulating factor
GM-CSF—granulocyte-marcrophage colony stimulating factor
PDGF—platelet derived growth factor
TGF-beta—transforming growth factor-beta
Hox—murine homeo-box complexes 1, 2 and 3
AAT—alpha 1-antitrypsin
AGP-A—alpha 1-acid glycoprotein
AFP—alpha-fetal protein
CRP—C-reactive protein
GRP—gonadotropin-releasing hormone
MBP—myelin basic protein
SOD Cu/Zn—copper zinc superoxide dismutase
VP—vassopressin
WAP—whey acidic protein
REN-2—renin 2
fused two pieces of DNA which are ligated together to form a single continuous piece
viral gene product—a protein from a viral gene, e.g., TIF gene

SUMMARY OF THE INVENTION

The present invention provides a two tiered system of gene regulation designed for use in non-human transgenic animals. In the first tier the gene of interest is directly regulated by a promoter which requires the presence of a transactivator for any appreciable expression. The tissue specificity, and the second tier of regulation in the invention, is provided by a TA line. The TA line carries the gene for the transactivator (TIF) regulated by a tissue specific promoter. The promoter for the TA transgene indirectly determines the site and time of expression from the IE regulated TR transgene. Only those animals with both the IE regulated TR transgene and an active TA transgene express the TR gene product. Because the TR gene requires the presence of a transactivator to induce expression, the invention provides a degree of control and allows for procedures which were not previously possible.

The invention thus relates to a Multiplex Gene Regulatory (MGR) system. Using the MGR system permanent lines of transgenic animals can be established for any gene of interest. The MGR system comprises two transgenic animal lines, a "transresponder" and a "transactivator" line. The transresponder (TR) line carries the gene of interest. This gene is fused to and regulated by a promoter sequence which is specifically activated only in the presence of a transacting factor. In the absence of the required transacting factor, there is little or no transcription of the transgene in the TR line. The transactivator (TA) line carries the gene which produces the required transactivator. The gene for the transactivator can be regulated by any available promoter sequence, including the promoter normally associate with the gene in the transgenic TR line. When heterozygous TR and TA lines are mated, approximately one quarter of the offspring inherit both of the transgenes. Only in these animals is the TR gene expressed. In the MGR system expression of the gene of interest is regulated by the presence or absence of the transactivator. Thus, the temporal, spatial and tissue specific pattern of TR gene expression is defined by the promoter which regulates the TA gene (see Table 1 hereinbelow). This two tiered system of regulation provides a highly flexible means for regulating transgene expression. The MGR System incorporates both the inducible character and the tissue specificity of the single tiered methods currently in use, but eliminates the unregulatable basal activity inherent to the one tiered systems. The MGR system is thus useful for analyses of gene function and advantageous for regulating commerical transgenic products.

The present invention concerns a transgenic non-human animal that carries integrated within its genome a transresponder transgene which comprises a gene of interest and a promoter sequence which is able to be regulated by a transactivator gene or a viral gene product and wherein in the absence of the transactivator gene or a viral gene product there is little or no expression of the gene of interest.

The present invention also concerns a transgenic non-human animal that carries integrated within its genome a transactivator transgene which comprises a promoter element fused to a coding sequence of a transactivator gene, the transactivator gene able to induce expression of a transresponder transgene and wherein expression of a transactivator gene product is not detrimental to developing embryos or adults.

The present invention is also directed to a transactivator gene fusion that comprises a promoter element fused to the coding sequence of a transactivator gene, the transactivator gene able to induce expression of a transresponder transgene, and wherein expression of a transactivator gene product is not detrimental to developing embryos or adults.

Still further, the present invention relates to a non-human transgenic animal offspring produced by the mating of a first transgenic non-human animal that carries integrated with its genome a transresponder transgene, the transresponder transgene containing a gene of interest and a second transgenic non-human animal that carries integrated within its genome a transactivator transgene, the first and second transgenic animals being of the same species and of opposite sexes, the offspring carrying the transresponder transgene from the first transgenic animal and the transactivator transgene from the second transgenic animal, in the absence of the transactivator transgene there being little or no expression of the transresponder gene and the expression of a transactivator gene product not being detrimental to developing embryos or adults.

The present invention also involves a process for producing a gene product comprising:

a. introducing into a first non-human animal a transresponder transgene containing a gene of interest and a promoter sequence, b. introducing into a second non-human animal a transactivator transgene, the first and second animals being of the same species and being of opposite sexes, c. mating the first and second animals so as to produce an offspring carrying the transresponder transgene and the transactivator transgene, in the absence of the transactivator transgene there being little or no expression of the transresponder gene, in the presence of the transactivator, the transresponder gene being induced and the expression of the transactivator gene product not being detrimental to developing embryos or adults, d. recovering the gene product from the offspring.

The present invention also concerns a process for producing a gene product comprising:

a. introducing into a non-human animal a transresponder transgene containing a gene of interest and a promoter sequence which is able to be regulated a transactivator gene or by a viral gene product, b. infecting the animal with a virus, the virus being able to activate the transresponder transgene, and c. recovering the gene product from the animal.

Viruses such as HSV-1, picornavirus, rhinovirus, hepatitis virus, reoviruses, arboviruses, rhabdoviruses, paramyxoviruses, orthomyxoviruses, togaviruses, arenaviruses, coronaviruses, bunyaviruses, parvoviruses, papovaviruses, poxviruses, poliomyelitis, aseptic menigitis, rabies, measles, vaccinia, influenza, Epstein-Barr virus, adenovirus, HIV viruses, cytomegalovirus and Norwalk type virus, just to mention a few, can be used in step b of the above described process. Included in the term virus is meant virus fragments that may or may not be infectious.

DETAILED DESCRIPTION OF THE INVENTION

MGR Components

Figure 1:
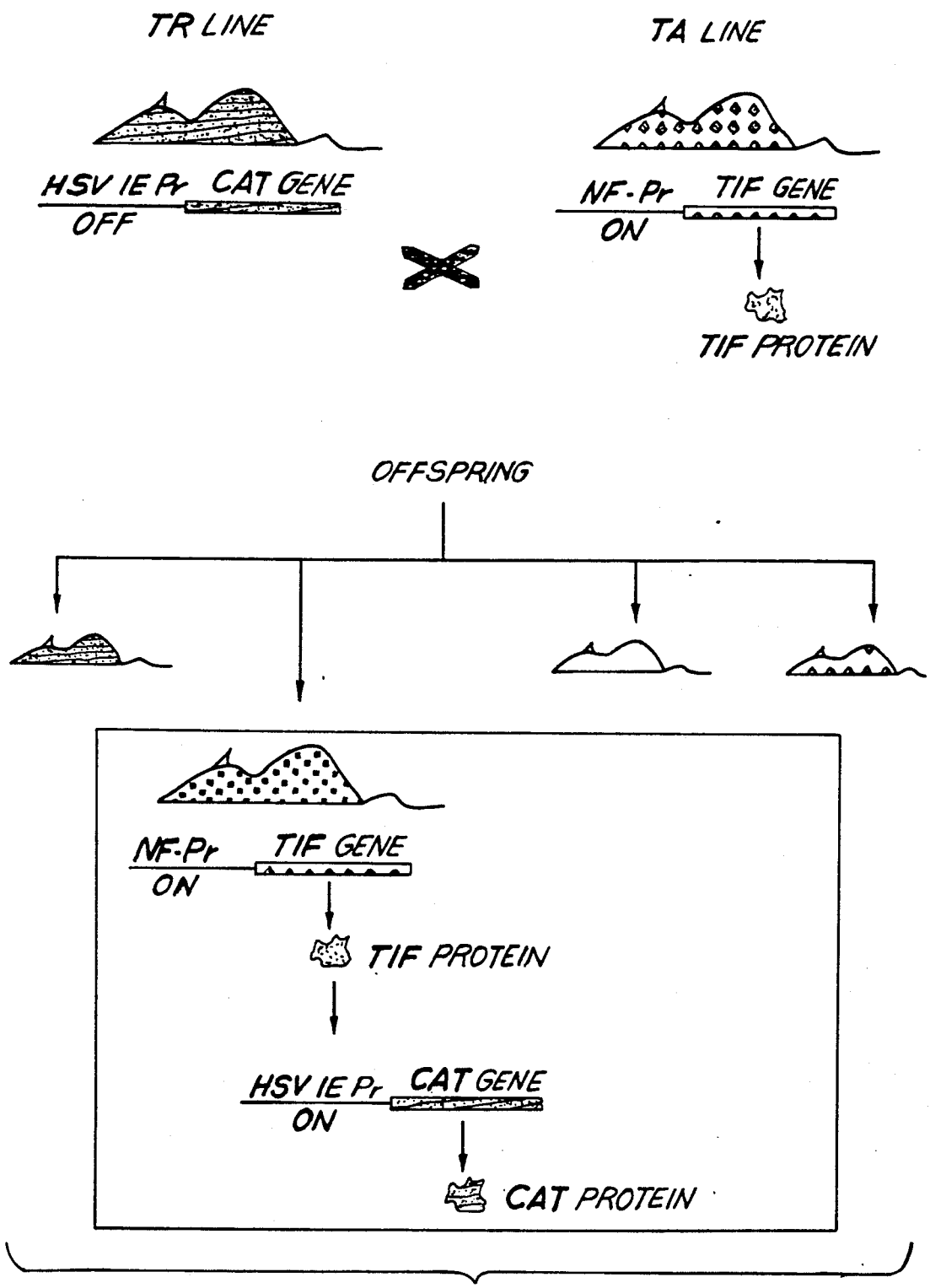
FIG. 1 is a schematic diagram of a method according to the invention.

The MGR system consists of a series of plasmid DNAs and two lines of transgenic mice. The plasmid DNAs are used in the construction of transgenic mice, and provide the essential components of the MGR system required for the analysis and regulation of other genes. The transgenic mouse (murine) lines IE-CAT and NFT use the HSV-1 IE promoter and TIF transactivator and have been used herein to demonstrate the MGR system, however, other animal lines and promoter transactivation pairs can be used. Table 1 hereinbelow is a non-limiting list of several known transactivators which can be employed in a MGR system.

TABLE 1

| Transactivator | Organism |
| --- | --- |
| IE175, IE110 | HSV-1 |
| GAL4, GCN4, HAP1 | Sacchromyces cerevisaie |
| BMLF-1, BMRF-1, BRLF-1 | EBV |
| E2 | CRPV, HPV, BPV |
| X gene | hepatitis B-virus |
| IE1 | Murine cytomegalovirus |

MGR Plasmids

Non-limiting examples of plasmids for use in the construction and operation of the MGR system are pP02, pPOH14, pCA15, pCAT, pIE, pIEZ, pTIF and pNF-TIF. The plasmids pIE and pTIF provide the IE promoter (pIE) and a TIF coding sequence (pTIF).

The plasmids pP02, pPOH14, and pCA15 have been described (O'Hare, P. and Hayward, G.S., (1985), "Three Trans-acting Regulatory Proteins of Herpes Simplex Viurs Modulate Immediate-early Gene Expression In a Pathway Involving Positive and Negative Feedback Regulation", J. of Virol., 56, 723–733; O'Hare, P. and Hayward, G.S., (1987), "Comparison of Upstream Sequence Requirements For Positive and Negative Regulation of Herpes Simplex Virus Immediate-early Gene by Three Virus-encoded Trans-acting Factors", J. of Virol., 61, 190–199).

The pPOH14, and pCAT plasmids provide the material used for the construction of the transgenic mouse lines IE-CAT. Plasmids pPOH14 and pCAT contain a fusion of the immediate early (IE) promoter from the ICP4 gene of HSV-1 to the bacterial reporter gene for chloramphenicol acetyltransferase (CAT) along with the splice and polyadenylation signals from SV40. The IE regulatory element is a 330 base pair 5' fragment of ICP4 which includes approximately 30 base pairs of 5' untranslated sequences, the TATA box and 3 TIF responsive cis-regulatory sequences. The sequence for this promoter fragment has been previously reported (Murchie, M.J. and McGeoch, D.J., (1982), "DNA Sequence Analysis of an Immediate-early Gene Region of the Herpes Simplex Virus type I Genome (Map Co-ordinates 0.950 to 0.978)", J. Gen. Virol., 62, 1–15).

IE-CAT gene fusion has been show in tissue culture cells to be activated by both HSV-1 infection and by transfection of the HSV-1 TIF gene (O'Hare and Hayward, 1985, supra, O'Hare and Hayward, 1987, supra). The fusion gene was excised from these plasmids and micro injected into single cell mouse embryos to produce the IE-CAT line of transgenic mice. The transgenic IE-CAT mouse lines are general purpose TR lines designed to test the MGR system.

Plasmid pTIF contains the 1.5 kb BamHI, AsuII fragment of pCA15 subcloned into a modified pGEM vector (Promega). This construct contains 60 bp of 5' untranslated leader, the entire TIF open reading frame and the endogenous polyadenylation signal. The vector provides multiple restrction sites to facilitate the construction of TA gene fusions. The entire TIF sequence has be reported (Pellett, P.E., McKnight, J.L.C., Jenkins, F.J. and Roizman, B., (1982), "Nucleotide Sequence Of a Protein Encoded in a Small Herpes Simplex Virus DNA Fragment Cabable of Trans-inducing Alpha Genes", Pro. Natl. Acad. Sci., 82, 5870–5874).

Plasmid pNF-TIF contains a 1.5 kilo base portion of the mouse neurofilament gene (NF-L) fused to the open reading frame of the HSV-1 TIF gene. The endogenous NF-L gene is one of a family of neuro-specific structural genes (Lewis, S.A. and Cowan, N.J., (1986), "Anomalous Placement of Introns in a Member of the Intermediate Filament Multigene Family: An Evolutionary Conundrum", Mol. and Cell Biol., 6, 1529–1539). The NF-L gene encodes a 68,000 dalton protein which is expressed on day 11 of mouse development and throughout the adult life (Julien, J.P., Meyer, D., Flavel, D., Hurst, J. and Grosveld, F., (1986), "Cloning and Developmental Expression of the Murine Neurofilament Gene Family", *Mol. Brain Res.*, 1, 243-250). The 1.5 kb NF-L regulatory element contains a TATA box and an unknown amount of 5' untranslated leader sequences. This regulatory region is fused to the TIF sequences from pTIF. The 3kb EcoRI, HindIII insert of pNF-TIF was microinjected into fertilized mouse eggs to produce the NFT transgenic mouse lines.

The plasmid pIE contains the 330 bp BamHI, SmaI regulatory region of ICP4 subcloned into a modified pGEM vector (Promega). This plasmid provides multiple restriction sites for easy construction of IE regulatored TR gene fusions.

The pIEZ plasmid is analogous to the pCAT plasmid described above except that it uses the beta-galactosidase gene of *Escherichia coli* in place of CAT as a reporter gene.

Characteristics of Transgenic Mice Carrying Both The TR and TA Transgenes (1) In the absence of transactivator there is little or no expression of the IE regulated gene in the TR line.
(2) The TR gene is activated through mating with a TA line.
(3) Expression of the transactivator gene product should not be detrimental to either the developing embryos or adults.

Animals Or Plants That Can Be Employed

The invention can be applied to warm or cold blooded animals and is not limited to rodents such as mice. Non-limiting examples of other animals that can be used include pigs, monkeys, goat, sheep, horses, cows, chickens and turkeys. Thus the MGR system can be applied, for example, to the development of transgenic livestock for the production of therapeutic gene products. The invention can be applied to lower eukaryots and those plants which can be regenerated from protoplast cultures. This includes most dicotyledonous plants and some monocotyledons such as wheat, corn and rice.

Transresponder Transgene

Basal TR gene expression

Figure 2:
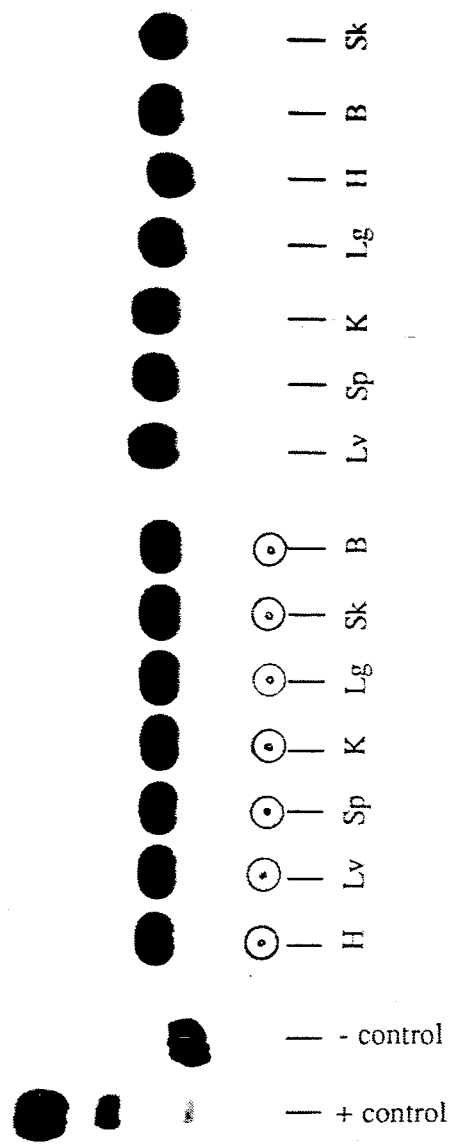
FIG. 2 is a photograph depicting basal CAT activity in TR lines IE-CAT 8 and IE-CAT 35.

CAT has been utilized herein as a target gene to test the MGR system. CAT is commonly used to assay the activity of promoter elements both in tissue culture and transgenic systems. This gene is advantageous because of a highly sensitive enzymatic assay which detects the CAT gene product (Gorman, C.M., Moffat, L.F. and Howard, (1982), "Recombinant Genes Which Express Chloramphenicol Acetyltransferase in Mammalian Cells", *Mol. Cell. Biol.*, 2, 1044-1051). To determine the basal activity level of the IE-CAT gene fusion, CAT assays were conducted on a spectrum of newborn tissue samples. FIG. 2 demonstrates that there is little or no CAT activity in two of the transgenic TR lines (IE-CAT8 and 35). Even when a vast excess of protein is used in the CAT assay, there was encountered difficulty in detecting a significant level of CAT activity in these animals. The basal level of CAT activity in two other TR lines has been analyzed. All four lines exhibit little or no CAT activity in any of the tissues tested.

IE promoters

The size of the IE promoter influences the basal and induced levels of gene activity. A non-limiting example of a promoter that can be used in the invention is a 330 bp IE promoter fragment. O'Hare, P. and Hayward, G.S., (1987), *J. of Virol.*, 61, 190-199 have demonstrated in tissue culture cells that both smaller and larger fragments form the ICP4 regulatory region exhibit quantitatively different levels of basal and induced activity. In general, larger fragments exhibit lower basal and high induced activity levels then smaller pieces. However, ICP4 promoter fragments much larger then the 330 bp element contain a second overlapping and divergent promoter element. The presence of this element which is oriented in the opposite direction form the ICP 4 promoter is probably disadvantageous for use in transgenic animals. The smaller IE promoter fragments which can be isolated from pIE may, however, be required for some gene fusions in order to maintain an acceptably low level of basal activity. It is also possible to use promoters from the other HSV immediate early genes.

Transactivation

Without a Transactivator Transgene

Figure 3:
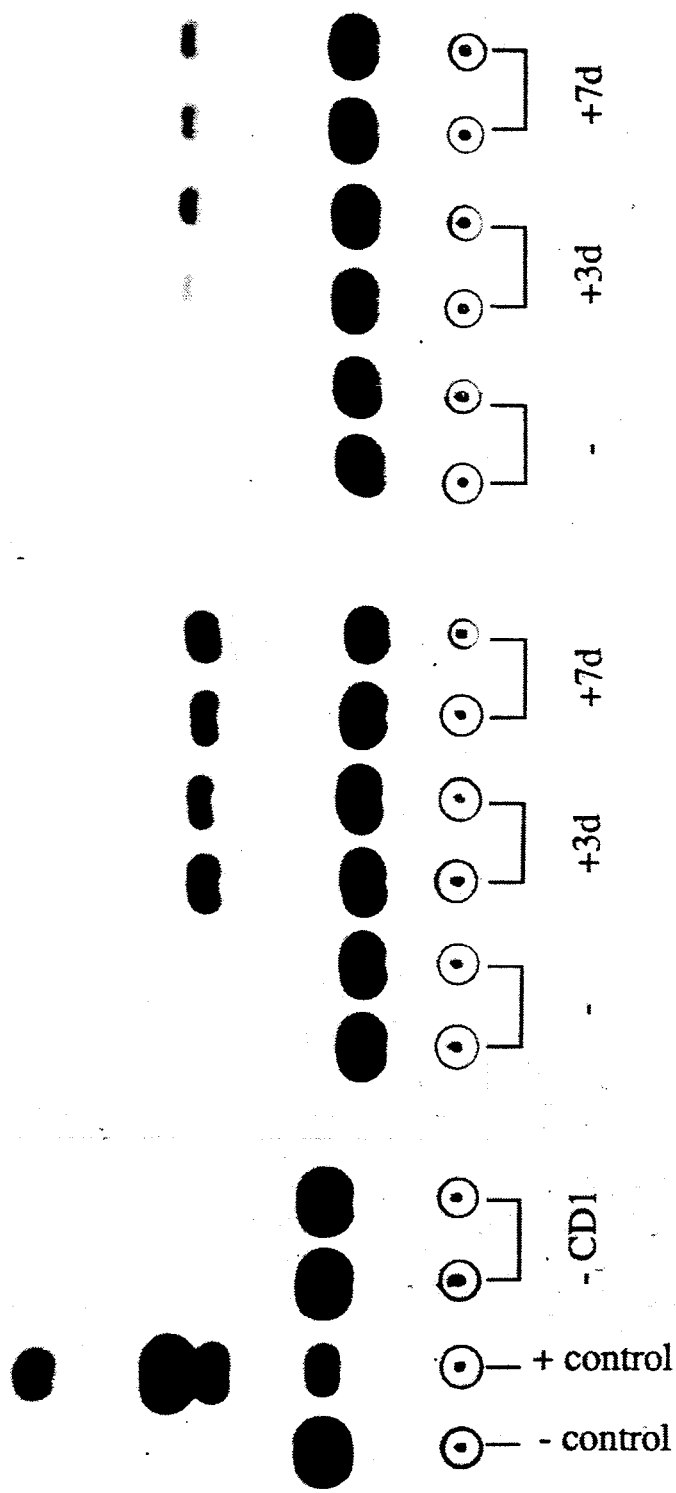
FIG. 3 is a photograph depicting CAT induction by HSV-1 infection.

To demonstrate that the IE-CAT gene present in the TR lines is still active adult mice were infected with HSV-1 by ocular scarification. O'Hare and Hayward (1985), supra had previously demonstrated that the IE-CAT gene fusion is strongly activated in tissue cultures cells when those cells are infected with HSV-1. An analogous experiment was conducted except that transgenic animals were used instead of tissue culture cells. FIG. 3 shows the results of CAT assays on eye tissue at three and seven days post infection. The infected transgenic animals exhibit an easily detected level of CAT activity. Uninfected transgenic and non-transgenic animals exhibit no CAT activity. This experiment demonstrates the inducible character of the IE-CAT transgene. Similar results were obtained with the IE-CAT33 and 38 TR lines.

With a Transactivator Transgene

Figure 4A:
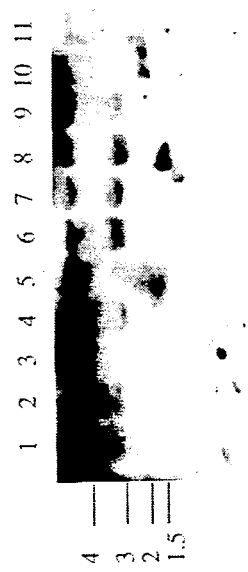
FIG. 4A is a photograph of the results of a Southern blot hybridization analysis of offspring from the transactivation of IE-CAT 8 mice by the NFT4 TA line.
Figure 4B:
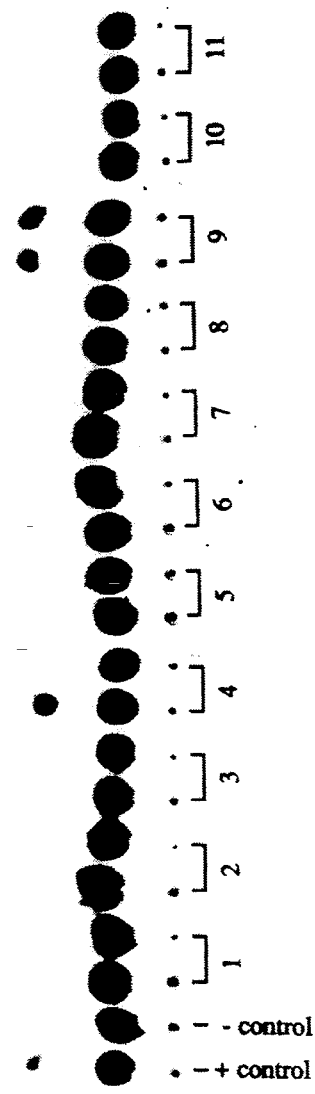
FIG. 4B is a photograph of CAT assays on brain (left) and spinal cord (right) from samples from the offspring described in FIG. 4A.

A final test of the MGR system is to activate CAT in the transgenic IE-CAT line by mating with a TA line. For this experiment a TR line, homozygous for the IE-CAT8 transgene was mated to a NFT male. This male was the original transgenic "founder" animal which apparently contained two unique integration sites. Only one of these integration sites expressed the TIF gene product. Seven of the eleven offspring inherited a NF-TIF transgene (FIG. 4A). Four of these animals contained the active NF-TIF gene and all exhibited CAT induction in samples from the brain and spinal cord. No CAT activity was detected in the offspring with the inactive NF-TIF transgene or in the absence of a NF-TIF transgene (FIG. 4B). These experiments clearly demonstrate the MGR system.

Effects of TIF expression

Due to the large size of the mouse genome it is likely that the TIF protein may induce expression from some endogenous mouse genes (O'Hare, P. and Goding, C.R., (1988), "Herpes Simplex Virus Regulatory Elements and the Immunoglobin Octamer Domain Bind a Common Factor and Are Both Targets for Virion Transactivation", *Cell*, 52, 435-445). This induction could result in undesirable side effects such as developmental abnormalities, sterility, or cancers. Whether these side effects appear probably depends on the time and site of TIF expression. It is significant then that the NFT line, which is likely to express TIF throughout the central nervous system, breeds well and has no apparent health problems. As of the filing date hereof, applicants' oldest NFT animals were 9–12 months old and they exhibit no sign of deleterious effect from TIF expression.

Using a different promoter, TIF expression was initiated at an early stage of mouse development (8.5 days) in a variety of mesodermal tissues (data not shown). These mice were also healthy and breed well. In contrast it has been attempted to make a TA line using a chick beta-actin promoter fused to TIF. The beta-actin promoter is a strong regulatory element which should be active throughout development in nearly all cell types. Apparently the beta-actin-TIF construct was lethal since it was not possible to produce any transgenic animals. This suggests that TIF expression beyond a certain level or in some tissue/stages cannot be tolerated during mouse developmental.

Model for MGR System

Although any number of different transactivator promoter pairs with the characteristics described herein can be used in the invention, an MGR system described herein was based on the well documented transactivation of Herpes Simplex Virus type 1 (HSV-1) immediate early (IE) genes (Hayward, G.S. and Sugden, B., (1986), "Herpesviruses" I. Genome Structure and Regulation. II. Latent and Oncogenic Infection by Human Herpesviruses", Cancer Cells 4. DNA Tumor Viruses: Control of Gene Expression and Replication, Butshan, M., Grodzicker, T., Sharp, P., ed., Vol. 4, 59–63). All of the five IE genes of HSV-1 have promoter regulatory sequences which are activated in trans by the HSV-1 gene product TIF (Mackem, S. and Roizman, B., (1982), "Structural Features of the Herpes Simplex Virus Alpha Genes 4, 0, and 27 Promoter-Regulatory Sequences Which Confer Regulation on Chimeric Thymidine Kinase Genes", *J. of Virol.*, 44, 939–949; Mosca, J.D., Reyes, G.R., Pitha, P.M. and Hayward, G.S., (1985), "Differential Activation of Hybrid Genes Containing Herpes Simplex Virus Immediate-early or Delayed-early Promoters After Superinfection of Stable DNA-Transfected Cell Lines", *J. of Virol.*, 56, 867–878; O'Hare and Hayward, (1985), *J. of Virol.*, 56, 723–733). This transactivation is specific for a cis- regulatory element present in one or more copies in each of the IE promoters.

Transactivation by TIF requires the cis-regulatory sequences in the IE promoters, the TIF protein and some uncharacterized cellular products (Kristie, T.M. and Roizman, B., (1987), "Host Cell Proteins Bind to the Cis-acting Site Required for Virion-mediated Induction of Herpes Simplex Virus 1 Alpha Genes", *Proc. Natl. Acad. Sci.*, 84, 71–75; Preston, C.M., Frame, M.C. and Campbell, M., (1988), "A Complex Formed Between Cell Components and an HSV Structural Polypeptide Binds to a Viral Immediate Early Gene Regulatory DNA Sequence", *Cell*, 52, 425–434; O'Hare and Hayward, 1987, J. of Virol., 61, 190–199). The TIF product is not a DNA binding protein. Instead transactivation appears to result when TIF forms a protein/DNA complex with one or more endogenous host factors.

Promoters

The MGR system of the invention makes no restrictions on the type of promoter used to regulate the transactivator. In FIG. 1 the murine neurofilament promoter was used to regulate the HSV-1 TIF gene (NF-TIF). Table 2 hereinbelow provides a non-limiting list of other promoters and their tissue specificity which are currently available and which can be used in the MGR process.

TABLE 2

| Promoter | Tissue |
| --- | --- |
| MBP, GRH, VP | Brain |
| Crystallin | eye |
| beta-lactoglobin, WAP | Mammary epethelium |
| Protamine | Spermatids |
| Elastase, Insulin Ren-2, CRP | Pancreas |
| AAT, AGP-A | Liver |
| AFP | Yolk sac |
| beta-globin | erythroid cells |
| kIg, uIg | B-cells |
| M-MuLV LTR | Macrophages |
| collagen, vimentin | connective tissue |
| alpha-Actin, myosin light chain | Muscle |
| H-2(HLA), beta-2-microglobin, SOD Cu/Zn | Many tissues |
| Hox, Intl | Developing CNS |

Modification of TIF

The level of induction from the IE regulated transgene is influenced by a number of factors. The site of integration in the mouse genome and the number of tandemly repeated copies influence both the basal and induced level of gene activity. These factors are beyond control. A major modification of the MGR system which will enhance the level of IE induction involves maximizing the stability of the TIF transcripts. The TIF gene in pTIF contains 60 bp of 5' untranslated leader, the TIP open reading frame and the endogenous polyadenylation signals. This gene, as isolated from the HSV genome produces an unspliced mRNA.

Brinster, R.L., Allen, J.M., Behringer, R.R., Gekinas, R.E. and Palmiter, R.D., (1988), "Introns Increase Transcriptional Efficiency In Transgenic Mice, *Proc. Natl. Acad. Sci.*, 85, 836–840 have shown that the presence of one or more introns enhances the transcriptions activity of genes introduced into transgenic mice. By supplying an intron sequence to the TIF gene, plasmid pTIF-SV can be constructed by removing the endogenous TIF polyadenylation signals and replacing them with a splice and polyadenylation sequence from SV40. This modified TIF gene should, when fused to a promoter, exhibit higher transcriptional activity and produce mRNA messages of greater stability. This will provide a major enhancement to the level of induced IE regulated gene activity.

Characterization of TA lines

It is important to accurately characterize the temporal and spatial patterns of TA gene expression. The IE-CAT TR lines of the invention are useful for determining the temporal pattern of transactivation in the offspring of a TR by TA cross, but it is difficult to localize the spatial patterns of CAT activity in these animals. To facilitate a spatial analysis of transactivation the pIEZ plasmid was constructed. This plasmid contains the *E. coli* beta-glactosidase gene fused to the IE promoter. A simple histochemical stain is available for visualizing beta-galactosidase activity in whole mounts and section of developing mouse embryos (Sanes, J.R., Rubenstein, J.L.R. and Nicolas, J.F., (1986), "Use of a Recombinant Retrovirus to Study Post-implantation Cell Lineage in Mouse Embryos", *EMBO*. 5, 3133-3142). Together these two TR lines provide a rapid and accurate method of characterizing TA activity.

Other Transactivator/Promoter pairs

The MGR system provides a high level of control for the expression of transgenes in transgenic animals. This level of control is achieved by using a transactivator/promoter pair in a two tiered system of regulation. There are two fundamental criteria for this approach to work. The promoter should have a low basal activity level in the absence of the transactiator, and expression of the transactivator should not be deleterious to the animal.

To augment the present system it may be possible to use the GAL4 transactivator from *Sacchromyces cerevisiae*. GAL4 is a DNA binding protein which activates transcription in yeast by binding to the galactose upstream activating region or to a synthetic 17bp consensus sequence (Giniger, E., Varnum, S.M. and Ptashne, M., (1985), "Specific DNA Binding of GAL4, a Positive Regulatory Protein of Yeast", Cell, 40, 767-774).

Using tissue culture cells two groups have demonstrated that GAL4 can transactivate chimeric genes containing either the yeast galactose upstream activating region or the synthetic 17-mer in mammalian cells (Kakidani, H. and Ptashne, M., (1988), "GAL4 Activates Gene Expression in Mammalian Cells", Cell 52, 169-178); Webster, N, Jin, J.R., Green, S., Hollis, M. and Chambon, P., (1988), "The Yeast UAS$_G$ is a Transcriptional Enhance in Human Hela Cells in The Presence of the GAL4 Trans-activator", Cell 52, 169-178). The effects of GAL4 expression in transgenic mice are unknown.

The TIF/IE based MGR system can be modified in a relatively simple way to incorporate GAL4 as an alternative transactivator. The synthetic 17bp GAL4 binding site could be included in the IE promoter element. This modified IE element is likely to have a similarly low level of basal activity and should be inducible using either TIF or GAL4 as a tranactivator. If GAL4 expression is well tolerated by the developing animal, e.g, mouse, this modification would extend the utility of the MGR system by permitting transactivation using GAL4 in tissues or at developmental stages in which TIF expression is lethal. In addition the inclusion of GAL4 increases the complexity of experiments which could be conducted using the MGR system. For instance, a TR line with a modified IE transgene could be mated to a TA animal, e.g., mouse, carrying both TIF and GAL4 controlled by different promoters with different tissue specificities. The offspring would have specific transgene induction in two different tissues when both TIF and GAL4 are inherited, or in each tissue spearately when only one of the transactivators are present. The complexity of the experiment increases in a similar way when the TR line carries both modified and unmodified IE transgenes.

Transgenic Animal Lines and Their Uses

Transgenic animal lines according to the invention, e.g., IC-CAT and NFT mouse lines, will be useful in studying infection, e.g., Herpes Simplex viruses, and in the development of therapeutic agents. It has been demonstrated that the IE-CAT line will activate CAT expression in the presence of infective virus. This IE-CAT line therefore can be a useful monitor for HSV and related virus infection.

The IE-CAT line and other lines according to the present invention can be used to monitor the efficacy of experimental vaccines or other therapeutic agents. For instance, the IE-CAT line could be given an experimental vaccine and then challenged with HSV-1. The effectiveness of the vaccine can then be easily monitored and quantitated by simply assaying for CAT activity. Because the CAT assay is rapid and simple, this could reduce the cost of vaccine development. MGR systems according to this invention which utilize transactivator and promoter pairs from other viruses such as those listed in Table 1 could be developed for similar applications.

The NFT line can be used for testing and development of pharmaceuticals for the treatment of HSV infection. The typical Herpes infection is a cyclic pattern of active infection, during which the virus replicates, followed by period of latency. At intermittent periods and for reasons which are not clear, the virus emerges from the latent state and initiates a new round of active replication. The means by which the virus goes latent are not clear, however, it is known that the unenveloped capsids move from the primary site of infection along neuronal axons towards their cell bodies (Cook, M.L. and Stevens, J.G., (1973), "Pathogenesis of Herpetic Neuritis and Ganglionitis in Mice: Evidence for Intra-axonal Transport of Infection", *Infect Immun.*, 7, 272). It has been suggested that the axonal transport of the capsid away from the primary site of infection may limit the expression of viral immediate early genes by physically separating the DNA from the viral TIF gene product (Hayward, G.S. and Sugden, G., (1986), "Herpesviruses: I. Genome Structure and Regulation, II. Latent and Oncogenic Infection by Human Herpesviruses". In *Cancer Cells*, 4, DNA Tumor Viruses: control of gene expression and replication, Botchan, M., Grodzicker, T., Sharp, P. ed., Vol. 4, 59-93). If this is the case the NFT line which expresses TIF throughout the central nervous system should be unable to establish a latent infection. These animals can therefore provide a model system to study active HSV infection, and for the development of therapeutic reagents.

Gene Products and Animal Models

In developing the MGR system, the CAT gene was used as a reported gene. However, in practice, the CAT gene would normally be replaced with some other gene of interest. Because of the low level of IE promoter activity in the uninduced state, the MGR system can be used to regulate a wide diversity of genes including those which might adversely effect development. This capability renders the MGR system ideal for producing therapeutic gene products or for developing animal models to human diseases. Table 3 provides a non-limiting list of genes which could be used for these purposes.

TABLE 3

| Gene products | |
| --- | --- |
| GM-CSF | |
| FGF | |
| TGF-beta | |
| EGF | |
| Interleukin 1, 2 and 6 | |
| Tumor necrosis factor | |
| PDGF | |
| EPO | |
| Animal Models | Disease |
| oncogenes | various cancers |

TABLE 3-continued

| | |
|---|---|
| Factor VIII:C | Hemophelia A |
| Factor IX | Hemophelia B |
| Collagen I | Osteogenesis imperfecta |
| beta-globin | beta-Thalassemia, Sickle Cell anemaia |
| T-cell receptor alpha | Ataxia telangiectasia |
| Retinoic acid receptor, retinoic acid binding protein, Hox, Int-1 | Developmental-abnormalties |
| G-CSF | promyelocytic leukemia |

Unlike the use of inducible or tissue specific promoter regulatory systems, the MGR system requires the presence of two transgenes in the same animal to express the product. This is an important characteristic for potential manufacturers of transgenic livestock, since it provides a method to control the distribution of their transgenic product. To maintain a supply of animals, without buying more from the manufacturer, the purchaser would have to screen the DNA of the offspring using a Southern blot hybridization to track the TR and TA transgenes. This technique is reasonably sophisticated and not generally available to agriculturalists. It is believed that the MGR system is the only method which provides this capability.

Other lines according to the invention which use different promoter transactivator pairs to control the MGR system may also be used to monitor other infectious agents (see Table 3 herein).

Analyis of Development

The MGR system permits some experiments which were not previously possible using the current regulatory methods described above. Many of the genes which are thought to regulate development in mannals are expressed in specific spatial patterns during development. These genes are thought to encode proteins which regulate the expression of other developmental genes including other regulatory genes.

It is believed that disruptions in the pattern or changes in the level of expression for these genes will produce serious and possibly lethal developmental affects. Since natural mutations are not available, it is desirable to use transgenic mice to determine their developmental functions. To begin such an analysis one would like to answer some simple questions. What is the effect of expressing the gene in an inappropriate pattern? What is the effect of over expressing the gene in the normal pattern? Neither inducible promoters or tissue specific promoters would be of much help in this problem since they either lack the tissue specificity, or inducible characteristics required to control a potentially lethal gene. The MGR system however was designed to address this problem.

First the regulatory gene to be studied is split into two portions, the 5' regulatory sequences and the coding region. A TR line is made using the IE promoter to regulate the coding region, and a TA line is made using the 5' regulatory sequences to control TIF expression. By mating these two lines one can induce transgene expression in the normal spatial pattern, but now at quantitative levels which are determined by the degree of transactivation. By making a second TA line with a different tissue specificity one can target expression of the TR transgene to ectopic sites.

Environmental Safety Aspect

The MGR system, because it requires two genes to activate the gene of interest, provides an additional level of control with respect to environmental safety precautions. For instance, transgenic mice might be made which express a gene product that may be potentially dangerous to humans. Using the heretofore single tiered regulatory method, such an animal would represent an environmental safety concern, since it is possible that this transgenic animal may escape from the laboratory and pass the transgene into the animal population. While this scenerio is unlikely, because of laboratory containment systems and since laboratory animals do not exist or breed very well in the wild, it does represent a serious concern to our society. The MGR system of the invention thus provides an additional level of safety. Only the animal, e.g., mouse, with both the TA and TR genes would express the potentially dangerous gene product. If that animal escaped, and if it could breed with wild mice, most of the offspring would inherit only the TA or TR genes. Only about one in four would inherit both the TR and TA genes.

Detailed Description of Some of the Figures

FIG. 1 is representation of the MGR system. The TR line contains a fusion transgene regulated by the HSV-1 IE promoter from ICP4. In this representation the TR gene is the reporter gene CAT. When using the MGR process the CAT gene would normally be replaced with the gene of interest such as those listed in Table 3. The TR transgene is inactive in the TR line. The TA line carries the HSV-1 TIF gene regulated by a tissue specific promoter element. In this representation mouse neurofilament gene was used to control TIF expression in the TA line. In the MGR system, however, any promoter element (see Table 2) may be substituted to control TIF expression in the TA line. When the TR and TA lines are mated the offspring represent either the parental genotypes, inheriting either the TA or the TR transgene, inherit neither transgene, or inherit both the TR and TA transgenes (highlighted box). In the offspring which inherit both transgenes the transactivator TIF is expressed in a tissue specific pattern defined by the promoter in the TA transgene. In those tissues where the TIF gene product is present, the TIF product complexes with other cellular transcription factors and activates the IE promoter leading to CAT expression. In every other tissue of the mouse where no TIF product is present there is no expression from the TR transgene. In this representation the HSV-1 IE promoter and the TIF transactivator was used to control the MGR process. Other promoter transactivator pairs could be used for an MGR system (see Table 1), however, it is essential that there is little or no activity of the TR transgene in the absence of the transactivator and that expression of the transactivator not be detrimental to the developing embryo or adult animal.

FIG. 2 depicts basal CAT activity in TR lines IE-CAT8 and IE-CAT35. CAT assays were performed on newborn tissue samples by the method of Gorman et al (1982), supra. The positive control was a protein extract from mouse L cells transfected with pCAT. A 100 fold excess of protein was used in the tissue assays. No CAT activity was detected in the IE-CAT35 line. The liver and lung tissues of the IE-CAT8 line display a marginally detectable level of CAT activity. All other tissues in the IE-CAT8 line are negative. Abbreviations: heart (H), liver (Lv), spleen (Sp), kidney (K), lung (Lg), skin (Sk), and brain (B).

FIG. 3 depicts CAT induction by HSV-1 infection. Adult TR mice of the IE-CAT8 and IE-CAT35 lines were anesthetized with 6mg/100g Nembutal, infected by ocular scarification and direct intercranial injection of HSV-1. Samples from both left and right eyes were examined for CAT activity at 3 and 7 days post infection. Both TR lines exhibit CAT induction by 3 days. There is no significant basal CAT activity in the uninfected TR animals (−) or in the non-transgenic CD1 controls. The positive control is protein extracted from mouse L cells transfected with pCAT.

FIG. 4 depicts transactivation of IE-CAT8 mice by the NFT4 TA line. The NFT4 founder male was mated to an IE-CAT8 female which was homozygous for the IE-CAT transgene. FIG. A depicts Southern blot hybridization analysis of the eleven offspring. The DNA was digested with Pvu2 and the NF-TIF gene was detected using a radiolabelled probe to the NF-L promoter region. This probe detects both the NF-TIF transgene and a high molecular weight band which is derived from the endogenous NF-L gene. The NFT4 founder mouse contains two separate integration sites. One integration site produces a doublet near 3kb (offsprings 1, 6 and 8), while the second integration site has only a single band of approximately 3.3kb (offsprings 2,4,7, and 9). FIG. 4B depicts CAT assays on brain (left) and spinal cord (right) samples from each offspring. Offsprings 2,4,7, and 9 which inherited the 3.3kb NF-TIF integration site exhibit positive induction of CAT activity. All other integration sites are inactive. The positive control is a protein extract of mouse L cells transfected with pCAT.

The invention will now be described with reference to the following non-limiting examples.

EXAMPLES

Example 1: Plasmid isolation

A single colony of bacteria was inoculated into 250 ml of LB media containing 50 µg/ml ampicillin. The cells were grown overnight at 37° C. on a shaker then pelleted by spinning at 5,000 g at 4° C. for 15 minutes in a centrifuge. The pellet was thoroughly resuspended in 5 ml of 25 mM Tris-HCl, pH 8.0, 10 mM EDTA, 50 mM glucose, and 2 mg/ml lysozyme, and incubated on ice for 10 minutes. To this suspension 10 ml of freshly prepared 0.2M NaOH, 1% SDS was added, mixed by inversion and incubated on ice for 10 minutes. Then 7.5 ml of 3M potassium acetate pH 4.8 was added, mixed by inversion and incubated for 20 minutes at 37° C. The supernatant was transferred to a fresh tube and 50 µl RNase (1 mg/ml) was added and incubated for 20 minutes at 37° C. This solution was extracted twice with an equal volume of phenol:chloroform (1:1) and the DNA precipitated by adding 2 volumes of ethanol. The DNA pellet was recovered by centrifugation at 9,500 g for 30 minutes. The DNA pellet was resuspended in 30 ml of water, and 28.5 g of CsCl and 1 ml of ethidium bromide (10 mg/ml) was added. This solution was centrifuged in a VTi50 rotor at 49,000 rpm for 16 hours. The plasmid DNA was collected from the CsCl gradient using a 5 ml syringe. The DNA was extracted 3 to 4 times with an equal volume of isoamyl alcohol to remove the ethidium bromide. The DNA was dialyzed overnight against 2 liters of TE (pH7.5) and concentrated by ethanol precipitation.

Example 2: Plasmids and cloning

Figure 5A:
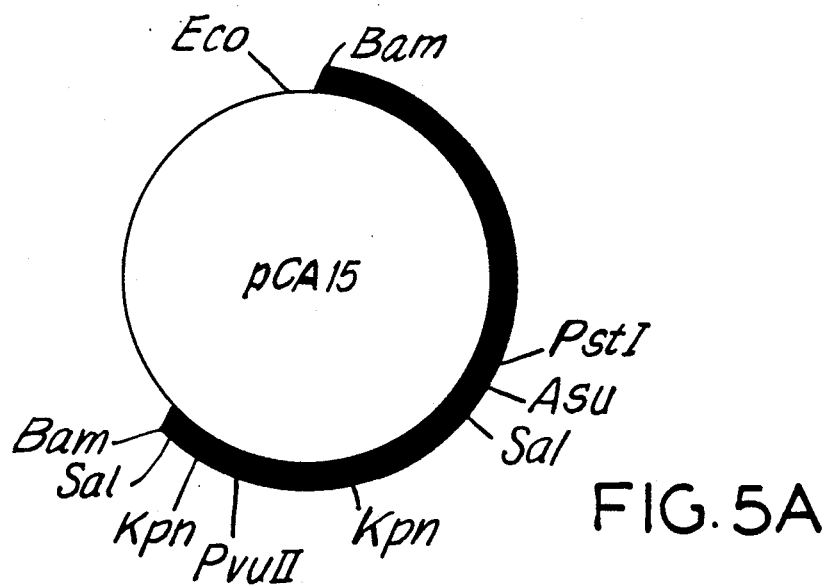
FIG. 5A is a schematic diagram of a partial restriction map for plasmid pCA15.
Figure 5B:
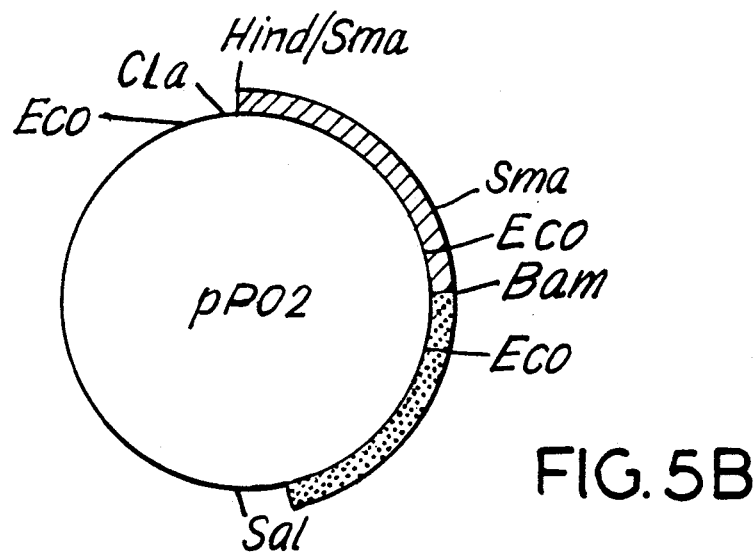
FIG. 5B is a schematic diagram of a partial restriction map for plasmid pP02.
Figure 5C:
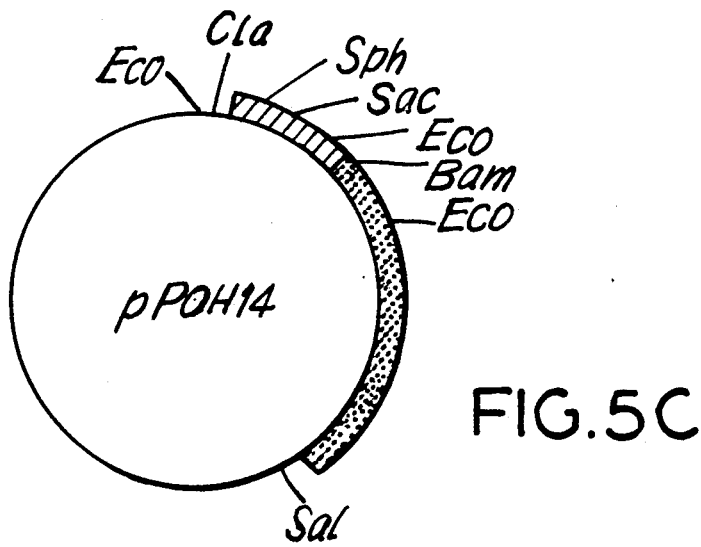
FIG. 5C is a schematic diagram of a partial restriction map for plasmid pPOH14.
Figure 6:
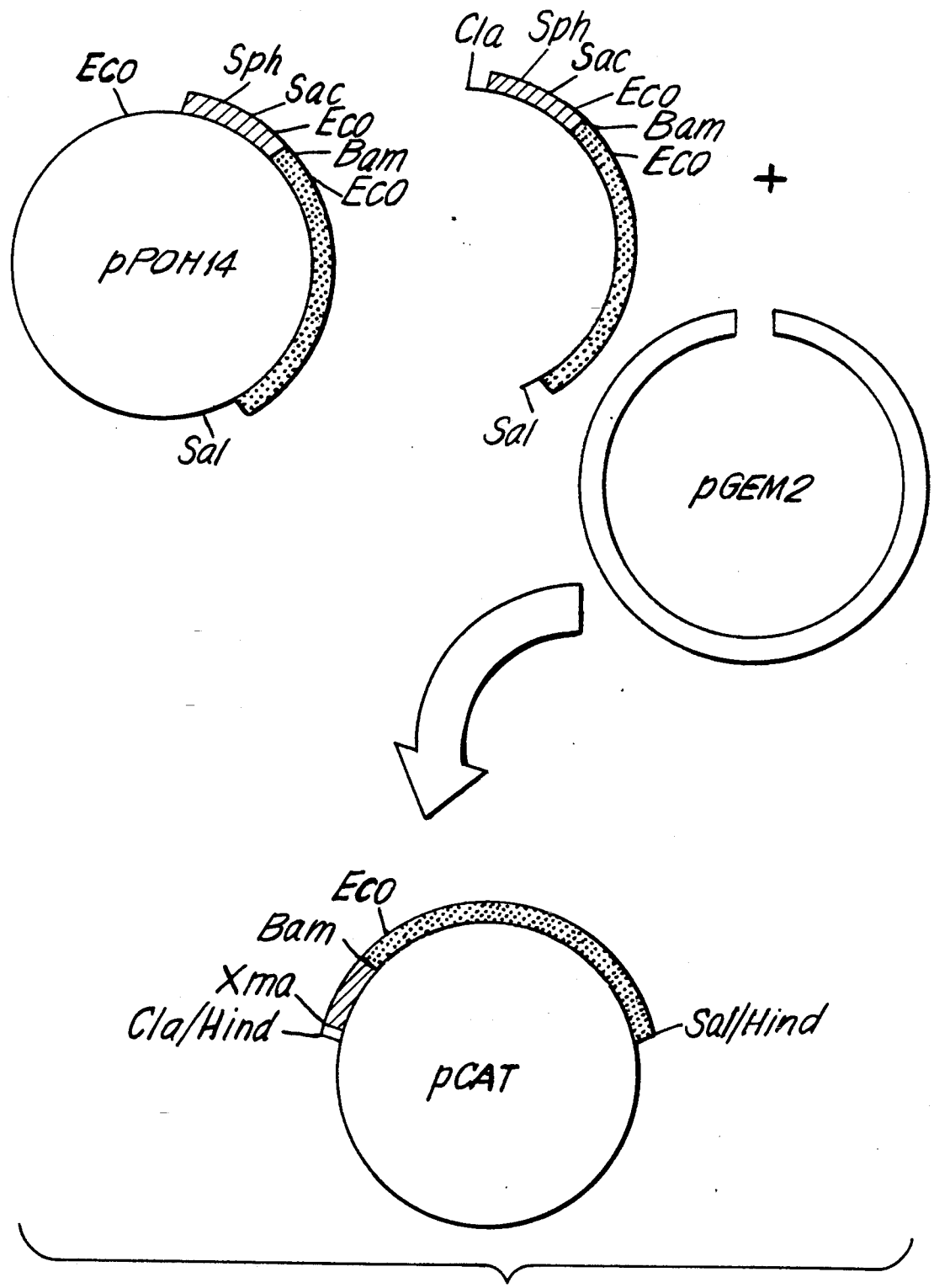
FIG. 6 is a schematic diagram for a process to produce pCAT.
Figure 7:
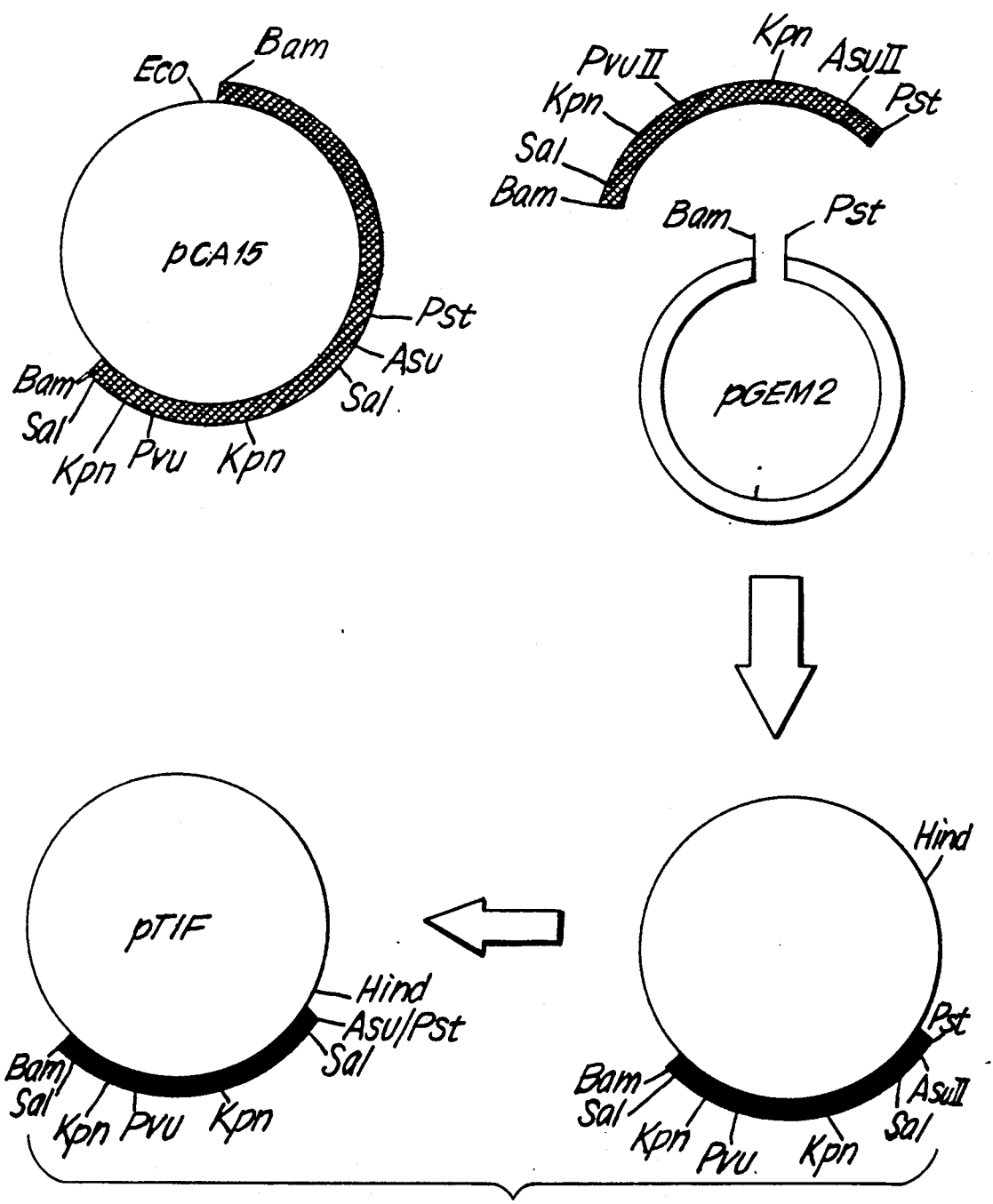
FIG. 7 schematically depicts a process to make plasmid pTIF.
Figure 8:
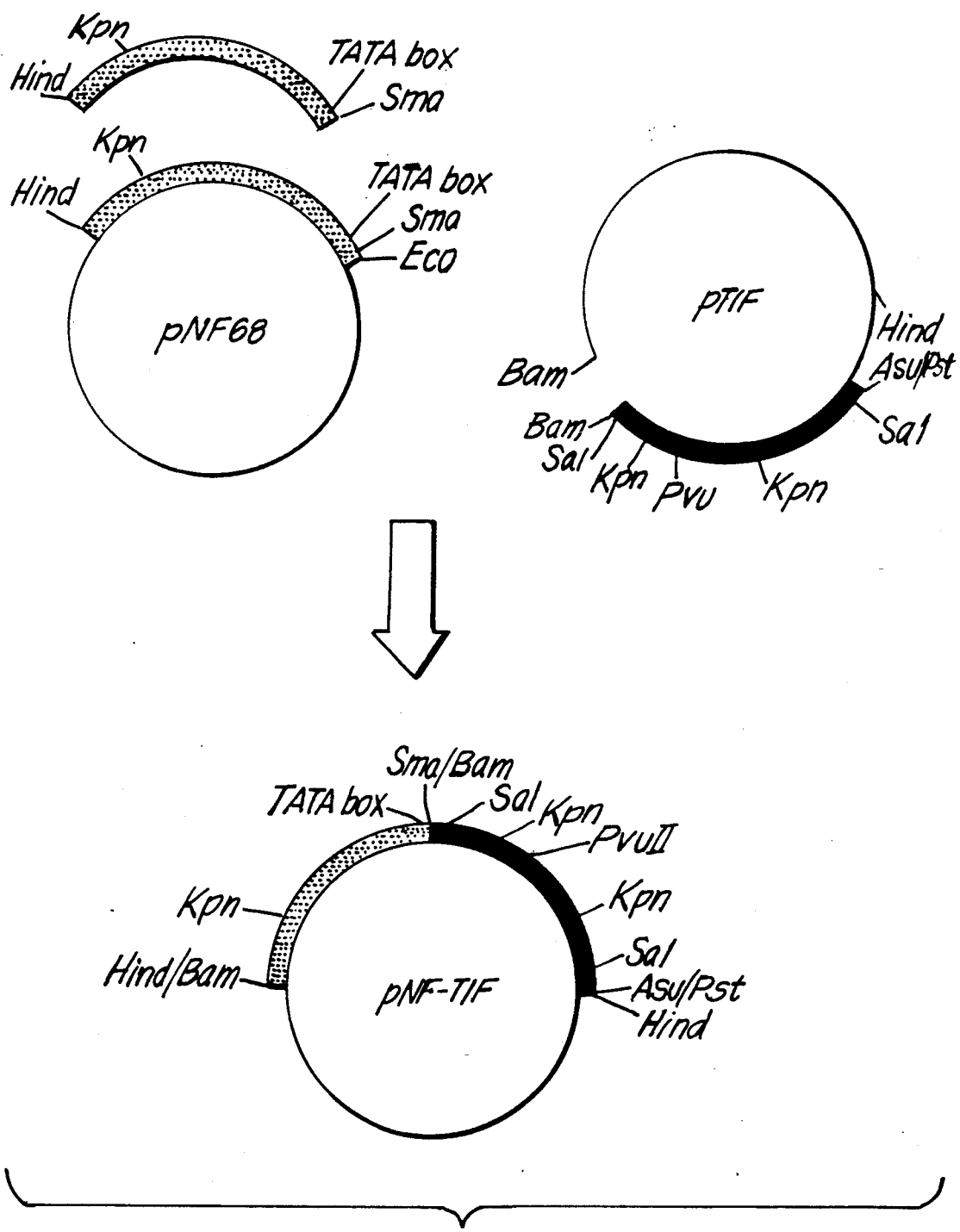
FIG. 8 schematically depicts a process to make plasmid pNF-TIF.
Figure 9:
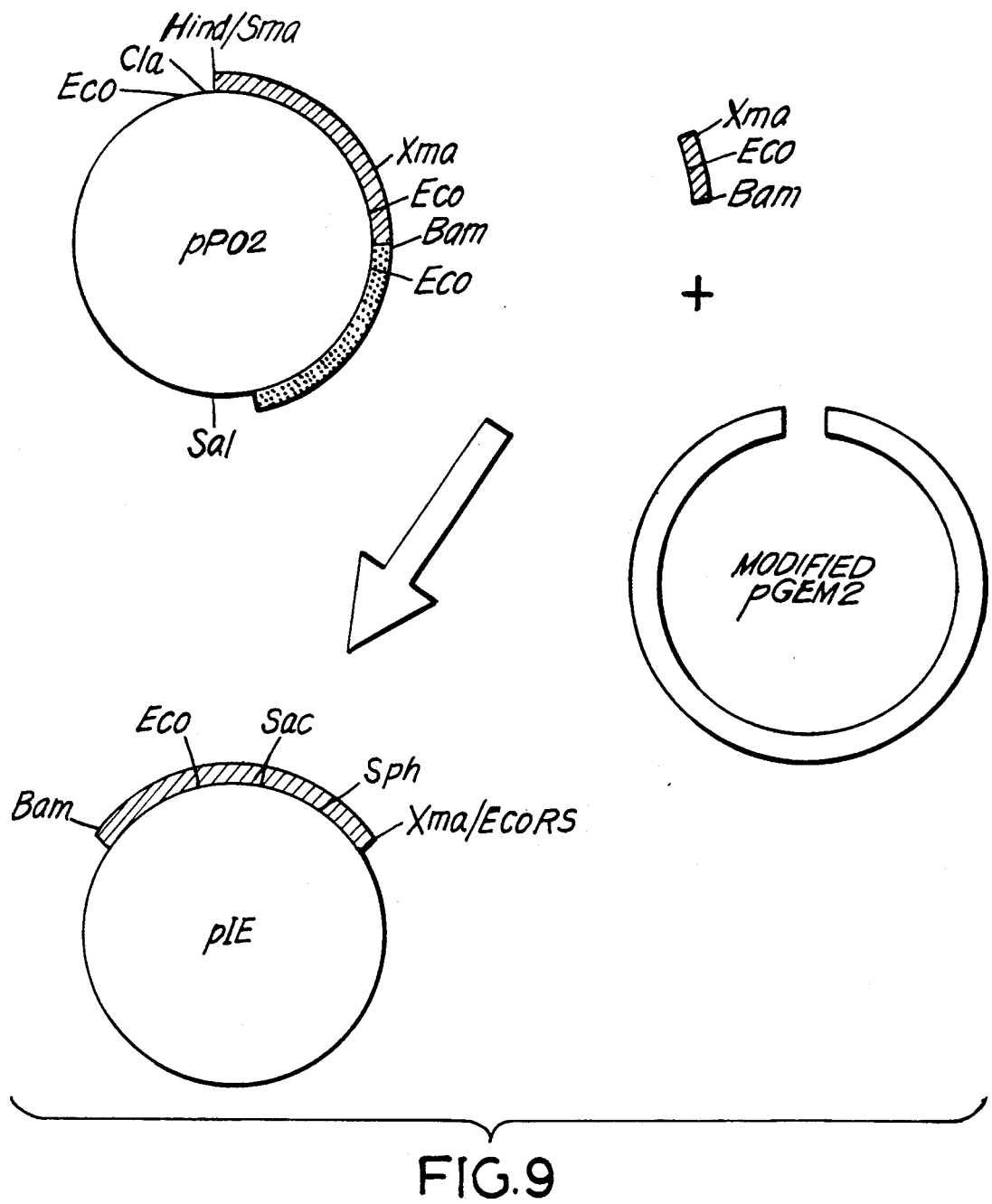
FIG. 9 schematically depicts a process to make plasmid pIE.
Figure 10:
FIG. 10 defines the symbols used in FIGS. 5 to 9.
Figure 10:
Figure 10:

Partial restriction maps of plasmids pCA15, pPO2, and pPOH14 are depicted in FIG. 5. These plasmids and their construction have been previously described (O'Hare and Hayward 1985, supra). To make the plasmid pCAT, the 2.0 kb ClaI, SalI fragment of pPO2 was isolated, end filled using Klenow and subcloned into the HincII site of pGEM2(Promega, Madison, Wisconsin, U.S.A.). This cloning process and a map of pCAT is presented in FIG. 6. The pTIF plasmid was made by subcloning the 1.7 kb BamHI, PstI fragment of pCA15 into the BamHI, PstI sites of pGEM2. The resulting plasmid was then digested with PstI and AsuII, end filed with T4 polymerase (IBI (International Biotechnologies, Inc.), New Haven, CT, U.S.A.) and religated, to produce pTIF. This cloning strategy is depicted in FIG. 7. The pNF-TIF plasmid was made by subcloning the 1.5 kb HindIII, SmaI fragment of pNF68 and blunt ligating it into the BamHI site of pTIF. This cloning strategy is depicted in FIG. 8. The pIE plasmid was made by subcloning the 330 bp SmaI, BamHI fragment from pPOH14 into the EcoRV, BamHI sites of a modified pGEM vector (FIG. 9). This modified pGEM is simply pGEM2 with the Blue script multiple cloning site.

In all of the cloning operations the gene fragments and vector sequences were gel purified from 0.8-1.0% nondenaturing agarose gels and concentrated using elutip columns following the manufacturer's recommended procedure. Vectors used in the cloning procedures were cut with restriction enzymes (IBI and Promega), dephosphorylated with calf-intestinal alkaline phosphatase (Boehringer Mannheim Biochemcial, Indianapolis, Inc., U.S.A.) and gel purified. For blunt end ligations the vector sequences were treated as described in *Molecular Cloning. A laboratory Manual*, Maniatis, T., Fritsch, E.F. and Sambrook, J., (1982), Cold Spring Harbor Press, Cold Spring Harbor, N.Y. For blunt ligations 5' overhand were end filled with Klenow. In this reaction 1 µg of DNA in 50mM Tris (pH 7.2), 10 mM MgS4, 0.1 mM DTT was mixed with 2nmoles of each dNTP, 1 unit of Klenow in a final volume of 20 µl. The reaction was incubated at room temperature of 30 minutes. The DNA was recovered either by gel purification or ethanol precipitation. For the conversion of 3' overhangs to blunt ends, T4 polymerase was used. In this reaction 1 µg of DNA in 33mM Tris-acetate (pH 7.9), 66mM potassium acetate, 10mM magnesium acetate, 0.5mM DTT was mixed with 1 µl of each dNTP (2mM) and 2 unites of T4 polymerase. The reaction (20 µl) was incubated at 37° C. for 5 minutes. The DNA was recovered as described above. All ligations were conducted at 3:1 molar ratios of insert:-vector with T4 ligase. Ligation reactions (50 ng) were transformed into competent DH5 cells and plated on LB agar containing 50 µg/ml ampicillin.

Example 3: Transgenic mice

The transgenic IE-CAT and NFT mice were made by the following procedure of Jon W. Gordon, George A. Scangos, Diane J. Plotkin, James A. Barbosa and Frank H. Ruddle, "Genetic Transformation of Purified DNA", *Proc. Natl. Acad. Sci. USA*, 77, 7380-7384, (1980): All mice were maintained on a 14:10 light-dark schedule (lights of at 10 p.m., on at 8 a.m.). Six-week-old females were induced to superovulate with 5 international units of pregnant mares' serum (Gestyl, Organon) at 4 p.m. followed 48 hours later by 2.5 international units of human chorionic gonadotropin (Pregnyl, Organon) and placed immediately with males for mating. B6D2F$_1$ female mice were mated with CD-1 male mice; CD-1 females were mated with B6D2F$_1$ males. On the same evening other mature CD-1 female mice were placed with vasectomized CD-1 male mice. On the morning after mating (day 0) all female mice were examined for vaginal plugs. Six-week-old females were killed at 2 p.m. on day 0 and their oviducts were removed into Krebs-Ringer bicarbonate-buffered medium supplemented with bovine serum albumin and hyaluronidase at 1 mg/ml. Oviducts were opened with forceps and the fertilized eggs with remaining follicle cells were expressed into the dish. After 1-2 minutes, eggs were removed and washed three times in 2 ml of culture medium equilibrated with 5% $CO_2$ in air at 37° C. Eggs containing pronuclei were identified under the dissecting microscope and placed in lots of 20 in a microdrop of equilibrated medium, which was placed in a 100-mm tissue culture dish and covered with mineral oil (Mallinckrodt 6358). Eggs were stored in this manner in the incubator until microinjected.

Microneedles were pulled from thin-walled no. 1211L Omega Dot tubing (Glass Co. of America) on a DK1 model 700° C. pipette puller. Holding pipettes were pulled by hand on a microburner from G-12 capillary tubing (Thomas), and fire polished on a Sensaur microforge. The tips of the microneedles were allowed to fill with plasmid suspension by capillary action and the barrels were then filled with Fluorinert (3M FC77). They were then secured in PE-190 intramedic tubing on a Leitz micromanipulator. Holding pipettes were also filled with Fluorinert and similarly secured in PE-90 tubing. The tubing was likewise filled with Fluorinert and attached to 1-$cm^3$ Hamilton syringes All manipulations were carried out on a Leitz microscope.

Tissue culture dishes containing the fertilized eggs were placed on the microscope and eggs were positioned by holding the pipette such that a pronucleus near the plasma membrane was close to the microneedle. The microneedle was inserted into the pronucleus and a solution of the 2 kb ClaI and SalI of pPOH14 (IE CAT) in the 3 kb EcoRI Hind III fragment of pNF-TIF (NFT) was injected to cause an approximate doubling of the pronuclear volume (approximately 1 pl). Eggs that survived microinjection were removed and stored in a 30-mm tissue culture dish containing 2 ml of equilibrated medium until all microinjections were completed. Injection of 40-60 embryos required 1-2 hours.

Plugged pseudopregnant CD-1 female mice were anesthetized with Nembutal at 6 mg/100 g of body weight. Ovaries were located through a dorsal incision. The ovarian bursa was torn away with no. 5 Dumont watchmaker's forceps, taking care not to rupture large blood vessels. The ostium of the oviduct was visualized under the dissecting microscope and a pipette containing 10-20 microinjected embryos was inserted into it. The eggs were expelled into the oviduct and the would was closed with wound clips. Three weeks after the offspring were born 2cm tail samples were taken and used for Southern blot hybridization to identifiy the transgenic offspring.

Example 4: DNA isolation

High molecular weight mouse DNA was isolated from 2 cm tail samples (adult mice) or from skin samples (newborn mice) using the following protocol. The tissue sample was placed in 700 µl of 50 mM Tris-HCL pH 8.0, 100 mM EDTA pH 8.0, 100 mM NaCl and 1% SDS. To this 35 µl of Proteinase K (10 mg/ml) was added and incubated at 50° C. overnight. The sample was extracted twice with 700 µl of phenol:chloroform and once with 700 µl of chloroform. The DNA was precipitated at room temperature with 2 volumes of ethanol, and recovered by using a sealed microcapillary tube to remove the DNA. The DNA was resuspended in 100 µl of water and quantified using a fluorimeter (Hoeffer).

Example 5: Probes and Southern Blot Hybridization

To identify transgenic offspring, tail DNA was analyzed by Southern blot hybridization. For each offspring, 15 µg of genomic DNA was digest overnight at 37° C. with PvuII (NFT) or BamHI (IE-CAT). The disgested DNA was fractionated on a 0.8% agarose gel, denatured in 1.5 M NaCl, 0.5M NaOH for 1 hour, neutralized in 1M Tris-HCl (pH 8.0), 1.5 M NaCl and blotted overnight on to nitrocellulose paper by capillary action. The nitrocellulose filter was baked at 80° C. for 1-2 hours prior to hybridization.

Either a 370 bp PstI fragment from the 1.5 kb BamHI, SmaI NF promoter or a 570 kb Kpnl SacI fragment of TIF was used as a probe to identify transgenic TA offspring. Similarly, the 280 bp BamHI EcoRI fragment of CAT was used as a probe to detect the IE-CAT line. All three fragments were subcloned into M13mp19 and a single strand radio labelled DNA probe was made by primer extension. To make the probe 1 µg of template DNA in 7mM Tris (pH 7.5), 7mM $MgCl_2$, 50 mM NaCl, 1mM DTT was mixed with 3ng M13 primer in a final volume of 10µl. The primer was annealed to the template by incubating the mixture at 65° C. for 2 minutes followed by a slow cooling to 30° C. To the annealed mixture 1 µl 0.1M DTT, 2 µl of cold dNTPs (a 1:1 mixture of 2mM dGTP and DTTP), 3 µl each of $^{32}P$ dCTP and dATP (800 Ci/mmol) and 1 µl of Sequenase was added and incubated at 37° C. for 30 minutes. After extension of the primer 2 µl of cold dNTPs (1:1:1:1 of 2mM dATP, dCTP, dTTP and dGTP) was added and incubated for 20 minutes. The salt concentration was then adjusted by adding 1 µl of 833mM NaCl and the DNA was cut with HindIII for 1-2 hours at 37° C. The single stranded probe was fractionated on a 4% polyacrylamide 8M urea gel, and the radio-labelled probe localized by exposing a piece of "KODAK XAR" film to the gel. The labelled probe was then cut out of the gel and the DNA electroeluted into a dialysis membrane.

The nitrocellulose filter was prehybridized for 2 hours at 45° C. in 40% formamide, 4X SSC, 10% dextran sulfate, IX Denhardht's, 0.05% SDS and 10 mM Tris-HCL (pH 7.5). Using fresh prehybridization buffer, the filter was hybridized for 16 hours at 45° C. with 200,000 cpm/ml of single stranded probe. Finally the filter was washed 3 times in 3X SSC, 0.1% SDS at 45° for 5 minutes and exposed to XAR film at −70° C. overnight.

Example 6: CAT assays

CAT assays were preformed on newborn tissue samples as described by Gorman et al (1982) supra. Tissue samples were removed from newborn animals, placed in 100 µl 0.25M Tris-HCl (pH 7.5) and frozen on dry ice. To extract the proteins the tissue samples were processed through 3 freeze thaw cycles with vigorous votexing and grinding of the tissue between each cycle.

After the extraction, the cellular debris was removed by a 4 minute centrifugation in an Eppendorf microfuge. The supernatant was then assayed for CAT activity exactly as described by Gorman et al (1982), supra, as follows: The assay mixture contained (in a final volume of 180 µl) 100 µl of 0.25 M Tris-hydrochloride (pH 7.5), 20 µl of cell extract, 1 µCi of [$^{14}$C]chloramphenicol (50 µCi/mmol; New England Nuclear Corp.), and 20 µl of 4 mM acetyl coenzyme A. Controls contained CAT (0.01 U; F.L. Biochemicals, Inc.) instead of cell extract. All of the reagents except coenzyme A were preincubated together for 5 minutes at 37° C. After equilibration was reached at this temperature, the reaction was started by adding coenzyme A. The reaction was stopped with 1 ml of cold ethyl acetate, which was also used to extract the chloramphenicol. The organic layer was dried and taken up in 30 µl of ethyl acetate, spotted on silica gel thin-layer plates, and run with chloroform-methanol (95:5, ascending). The thin-layer plates were autoradiographed overnight at room temperature using KODAK XAR film.

It will be appreciated that the instant specification and claims are set forth by way of illustration and not limitation, and that various modifications and changes may be made without departing from the spirit and scope of the present invention.

What is claimed is:

1. A transgenic mouse that carries in the genome of its somatic and germ cells a transresponder transgene which comprises a gene of interest operably linked to a promoter sequence which is regulated by a viral gene product of HSV-1.

2. A transgenic mouse according to claim 1, wherein said viral gene product is encoded by the TIF gene of HSV-1.

3. A transgenic mouse according to claim 1, wherein the promoter for the transresponder transgene comprises an IE promoter of HSV-1.

4. A transgenic mouse according to claim 2, wherein said gene of interest is the CAT gene.

5. A transgenic mouse that carries in the genome of its somatic and germ cells a transactivator transgene which comprises the TIF gene of HSV-1, operably linked to a promoter sequence.

6. A transgenic mouse according to claim 5, wherein the promoter for the transactivator transgene comprises a mouse NF-L promoter.

7. A process for expressing a gene of interest comprising:
   a. introducing into a first mouse a transresponder transgene containing the gene of interest operably linked to a promoter sequence which is regulated by a viral gene product of HSV-1,
   b. introducing into a second mouse a transactivator transgene comprising the TIF gene of HSV-1,
   c. mating the first and second mice so as to produce an offspring carrying the transresponder transgene and the transactivator transgene, and maintaining said offspring under conditions effective for the expression of said gene of interest 8. A process according to claim 7, wherein the transresponder transgene comprises a HSV-IE promoter fused to the CAT gene.

9. A process according to claim 7, wherein the transactivator transgene comprises the mouse NF-L promoter fused to the TIF gene of HSV-1.

10. A process for expressing a gene of interest comprising:
    a. introducing into a mouse a transresponder transgene containing a gene of interest operably linked to a promoter sequence which is regulated by a viral gene product of HSV-1,
    b. infecting said mouse with a HSV-1 virus, thereby activating the transresponder transgene and maintaining said mouse under conditions effective for the expression of said gene of interest.

11. A process according to claim 10 wherein said viral gene product is encoded by the TIF gene of HSV-1.

12. A process according to claim 10, wherein said gene of interest is the CAT gene.

* * * * *